US00PP18766P2

(12) United States Plant Patent
Hartman

(10) Patent No.: US PP18,766 P2
(45) Date of Patent: Apr. 29, 2008

(54) ***CALADIUM* PLANT NAMED 'CANDYLAND'**

(50) Latin Name: *Caladium×hortulanum*
Varietal Denomination: Candyland

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 11/648,872

(22) Filed: Dec. 29, 2006

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
(74) *Attorney, Agent, or Firm*—C. A. Whealy

(57) ABSTRACT

A new and distinct cultivar of *Caladium* plant named 'Candyland', characterized by its compact, upright and outwardly arching plant habit; vigorous, dense and bushy growth habit; strap-like leaves; and green, red and white-colored leaves.

4 Drawing Sheets

Botanical designation: *Caladium×hortulanum.*
Cultivar denomination: 'Candyland'.

BACKGROUND OF THE INVENTION

The present invention relates to a new and distinct cultivar of *Caladium* plant, botanically known as *Caladium× hortulanum,* commercially referred to as a strap-leaf *Caladium* and hereinafter referred to by the name 'Candyland'.

The new *Caladium* originated from a cross-pollination made by the Inventor in April, 2001, in Lake Placid, Fla. of the *Caladium×hortulanum* cultivar Lance Whorton, not patented, as the female, or seed, parent with the *Caladium× hortulanum* cultivar Gingerland, not patented, as the male, or pollen, parent. The new *Caladium* was discovered and selected by the Inventor as a single plant within the progeny of the stated cross-pollination in a controlled environment in Lake Placid, Fla. on Jun. 15, 2002.

Asexual reproduction of the new cultivar by tuber divisions in a controlled environment in Lake Placid, Fla. since Apr. 15, 2003 has shown that the unique features of this new *Caladium* are stable and reproduced true to type in successive generations of asexual reproduction.

SUMMARY OF THE INVENTION

The cultivar Candyland has not been observed under all possible environmental conditions. The phenotype may vary somewhat with variations in environment such as temperature and light intensity, without, however, any variance in genotype.

The following traits have been repeatedly observed and are determined to be the unique characteristics of 'Candyland'. These characteristics in combination distinguish 'Candyland' as a new and distinct cultivar of *Caladium:*

1. Compact, upright and outwardly arching plant habit.
2. Vigorous, dense and bushy growth habit.
3. Strap-like leaves.
4. Green, red and white-colored leaves.

In side-by-side comparisons conducted in Lake Placid, Fla., plants of the new *Caladium* differed from plants of the female parent, the cultivar Lance Whorton, in the following characteristics:

1. Plants of the new *Caladium* were more compact than plants of the cultivar Lance Whorton.
2. Plants of the new *Caladium* were denser and bushier in growth habit than plants of the cultivar Lance Whorton.
3. Leaves of plants of the new *Caladium* were wider than leaves of plants of the cultivar Lance Whorton.
4. Leaves of plants of the new *Caladium* were more red in color than leaves of plants of the cultivar Lance Whorton.

In side-by-side comparisons conducted in Lake Placid, Fla., plants of the new *Caladium* differed from plants of the male parent, the cultivar Gingerland, in the following characteristics:

1. Plants of the new *Caladium* were more compact and less vigorous than plants of the cultivar Gingerland.
2. Leaves of plants of the new *Caladium* were less undulate than leaves of plants of the cultivar Gingerland.
3. Plants of the new *Caladium* and the cultivar Gingerland differed in leaf coloration as plants of the cultivar Gingerland had white-colored venation.
4. Plants of the new *Caladium* had shorter leaf petioles than plants of the cultivar Gingerland.

Plants of the new *Caladium* can also be compared to plants of the cultivar Florida Sweetheart, disclosed in U.S. Plant Pat. No. 8,526. In side-by-side comparisons conducted in Lake Placid, Fla., plants of the new *Caladium* differed from plants of the cultivar Florida Sweetheart in the following characteristics:

1. Plants of the new *Caladium* were more upright than plants of the cultivar Florida Sweetheart.
2. Leaves of plants of the new *Caladium* were more rounded than leaves of plants of the cultivar Florida Sweetheart.
3. Leaves of plants of the new *Caladium* were more smoother than and not as undulate as leaves of plants of the cultivar Florida Sweetheart.
4. Plants of the new *Caladium* and the cultivar Florida Sweetheart differed in leaf coloration as plants of the cultivar Florida Sweetheart had pink-colored leaves.

BRIEF DESCRIPTION OF THE PHOTOGRAPHS

The accompanying photographs illustrate the overall appearance of the new *Caladium*. These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet comprises a side perspective view of a typical plant of 'Candyland' grown in a container.

The photograph on the second sheet comprises a close-up view of leaves of typical plants of 'Candyland'.

The photograph on the third sheet is a close-up view of a typical inflorescence of 'Candyland'.

The photograph on the fourth sheet is a close-up view of typical tubers of 'Candyland'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in 15-cm containers in Lake Placid, Fla. during the spring in a polyethylene-covered shadehouse and under conditions and practices which approximate those generally used in commercial *Caladium* production. During the production of the plants, day temperatures ranged from about 21° C. to 38° C., night temperatures ranged from about 10° C. to 21° C. and light levels about 8,000 foot-candles. Plants were about seven weeks from planting tubers when the photographs and the detailed description were taken.

Botanical classification: *Caladium×hortulanum* cultivar Candyland.

Parentage:

*Female, or seed, parent.*—*Caladium×hortulanum* cultivar Lance Whorton, not patented.

*Male, or pollen, parent.*—*Caladium×hortulanum* cultivar Gingerland, not patented.

Propagation:

*Type.*—By tuber divisions.

*Time to initiate roots, summer.*—About seven to ten days at 32° C.

*Time to initiate roots, winter.*—About two to three weeks at 24° C.

*Tuber description.*—Number of buds per tuber: About five actively growing buds/shoots and about twelve dormant buds. Height: About 2.8 cm. Diameter: About 3.6 cm. Texture: Thick, starchy; somewhat brittle. Color: Epidermis, 200A to 200B; interior, 2D. Root description/habit: Dense, thick and white fleshy roots with finer lateral roots.

Plant description:

*Plant/growth habit.*—Compact, upright and outwardly arching plant habit. Vigorous, dense and bushy growth habit; suitable for 10-cm to 25-cm containers. Mostly upright leaf petioles.

*Plant height, from soil level to top of leaf plant.*—About 20 cm.

*Plant height, from soil level to top of inflorescences.*—About 29 cm.

*Plant spread.*—About 32 cm.

*Cataphylls.*—Length: About 5 cm. Width: About 1.2 cm. Shape: Linear to elliptic. Apex: Acuminate. Base: Sheathing the stem. Color, outer surface: N170D streaks, N186A. Color, inner surface: 170D; faint streaks, N186A.

Foliage description:

*Length.*—About 15 cm.

*Width.*—About 9.5 cm.

*Shape.*—Ovate to lanceolate.

*Apex.*—Acuminate.

*Base.*—Sagittate to cordate.

*Margin.*—Entire; slightly undulate.

*Texture, upper surface.*—Smooth, glabrous.

*Texture, lower surface.*—Smooth, glabrous; glaucous.

*Venation pattern.*—Pinnate.

*Color.*—Developing leaves, upper surface: Margins: Darker than 137A. Center: Intervenal areas, 193D and lighter and more green than 137A, suffused with 47C to 47D; random spots, 48A to 48B and 46A. Venation: Laterals and midvein, 50C to 50D tinged with 147D; petiole attachment and adjacent veins, 60A to 59A. Developing leaves, lower surface: Margins: 191A. Center: Intervenal areas, 191A; random spots, 62A. Venation: Laterals and midvein, 147D faintly tinged with 62D; areas surrounding veins, 192D to 155C; at petiole attachment, 59B. Fully developed leaves, upper surface: Margins: Darker than 137A. Center: Intervenal areas, 193B to 193C, suffused with 47C to 47D; random spots, 48A to 48B and 46A. Venation: Laterals and midvein, 50C to 50D tinged with 147D; petiole attachment and adjacent veins, 60A and 59A. Fully developed leaves, lower surface: Margins: 191A. Center: Intervenal areas, 191A; random spots, 62A. Venation: Laterals and midvein, 147D faintly tinged with 62D; areas surrounding veins, 192D to 155C; at petiole attachment, 59B.

*Petiole.*—Aspect: Mostly erect, outwardly arching with development. Length: About 15.5 cm. Diameter, distal: About 3.7 mm. Diameter, proximal: About 1 cm. Strength: Strong; flexible. Color: 181B to 181C; streaks, N186A. Wing length: About 5.2 cm. Wing diameter: About 1 cm. Wing color, outer and inner surfaces: N170D; streaks, N186A.

Inflorescence description:

*Inflorescence arrangement.*—Hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about eight to nine weeks after growth commences. Inflorescences last about three days before fading; inflorescences persistent.

*Spathe.*—Length: About 9.1 cm. Width: About 2.7 cm. Shape: Ovate. Apex: Acute. Base: Tapering. Margin: Entire. Texture, upper and lower surfaces: Smooth, glabrous. Color: When developing, front surface: Upper two-thirds. 195B to 195C. Lower one-third:

147C flushed with tiny speckles of N79B. When developing, rear surface: Upper two-thirds: 194A. Lower one-third: 137C. Fully developed, front surface: Upper two-thirds: N155C; with development, 199D tinged with 145B. Lower one-third: 138B to 138C with tiny speckles of N79B; with development, 137C. Fully opened, rear surface: Upper two-thirds: N155B suffused with N181D. Lower one-third: 137C to 137D.

*Spadix.*—Length, entire spadix: About 4.8 cm. Length, male flower zone: About 2.7 cm. Length, sterile flower zone: About 1 cm. Length, female flower zone: About 1.1 cm. Diameter, male flower zone: About 7 mm. Diameter, sterile flower zone: About 6.8 mm. Diameter, female flower zone: About 6 mm. Shape: Columnar. Apex: Obtuse. Base: Obtuse. Aspect: Upright. Color: Immature, male zone: 157A. Immature, female zone: 157D. Mature, male zone: 155D. Mature, female zone: 155A.

*Female flowers.*—Quantity per spadix: About 55. Shape: Ovate to elliptic. Height: About 2 mm. Diameter: About 2 mm. Stigma color: 155A. Ovary color: 155A.

*Male flowers.*—Quantity per spadix: About 78. Shape: Obovate; inverted triangle. Height: About 3 mm. Diameter: About 3 mm. Anther color: 157D. Amount of pollen: Sparse. Pollen color: 11C.

*Scape.*—Length: About 19 cm. Diameter: About 4 mm. Strength: Sturdy; flexible. Aspect: Erect. Texture: Smooth, glabrous; glaucous. Color: 181B to 181C, streaks, N186A.

*Seed and fruit.*—Seed and fruit development has not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'Candyland' as illustrated and described.

* * * * *

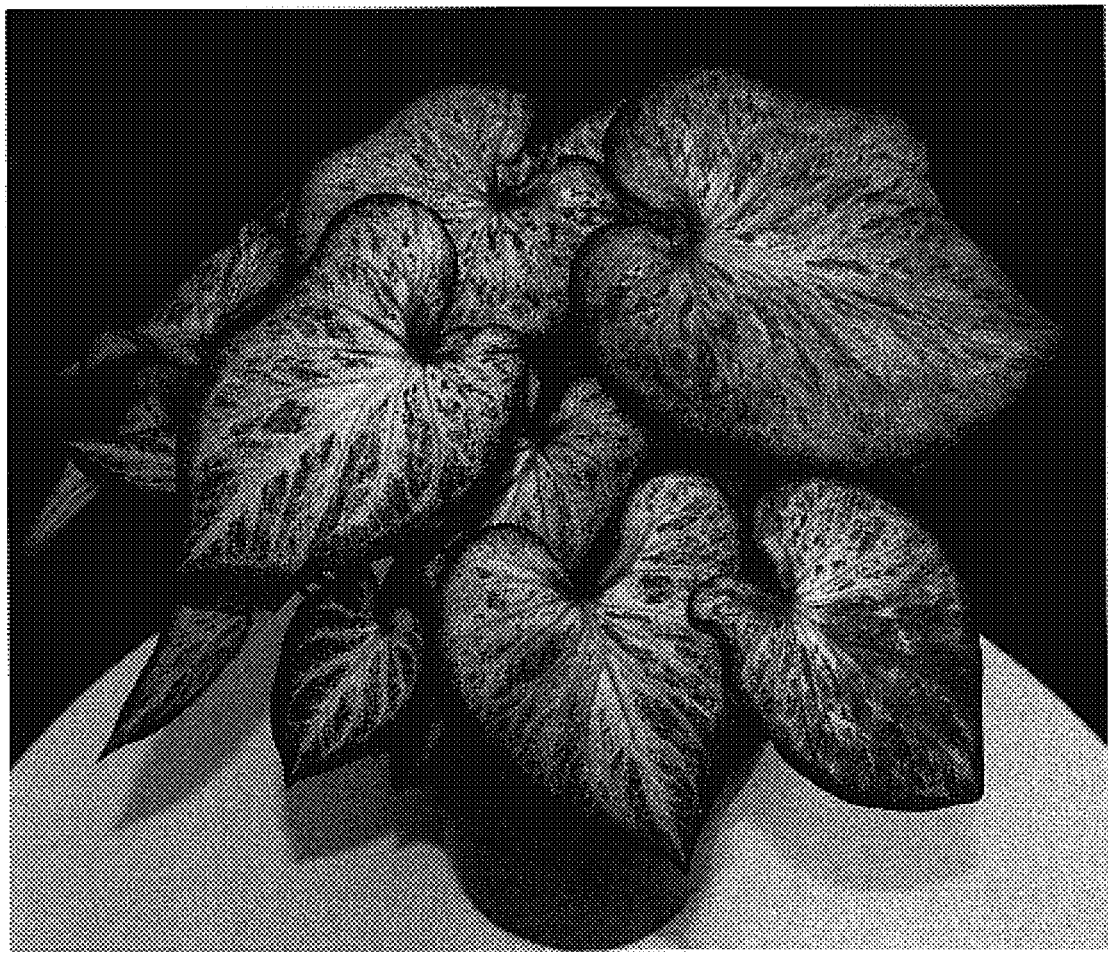

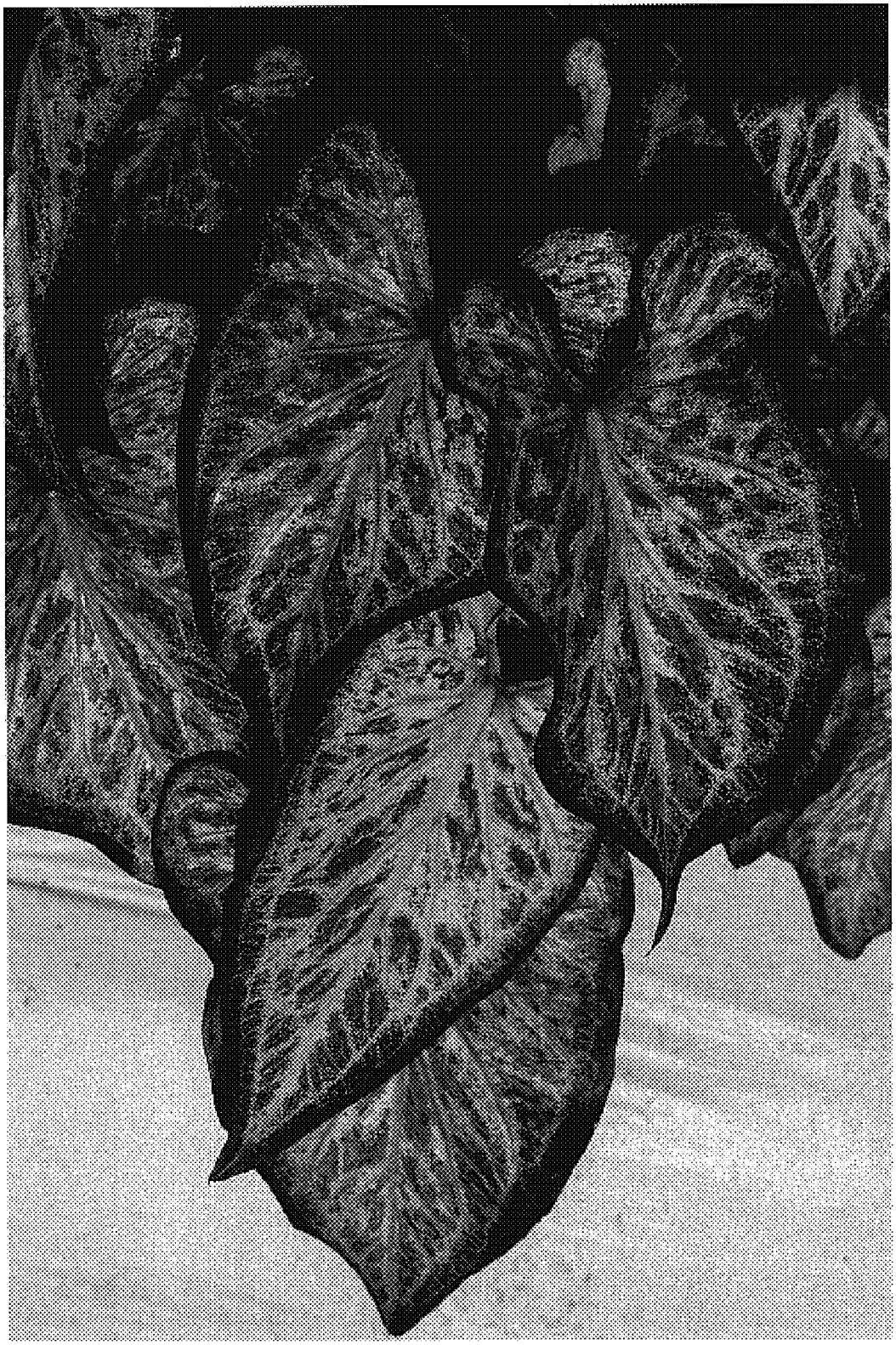

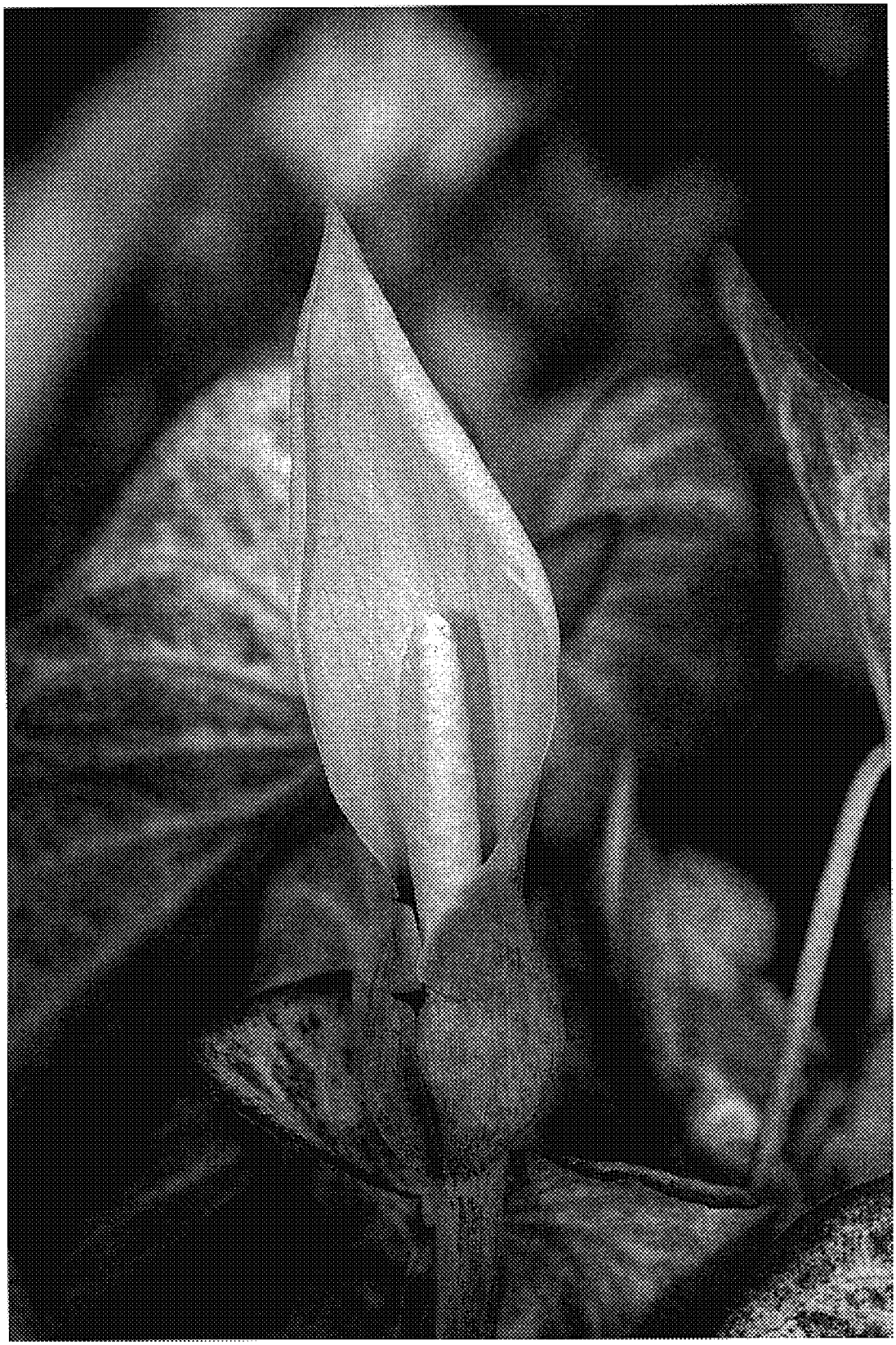

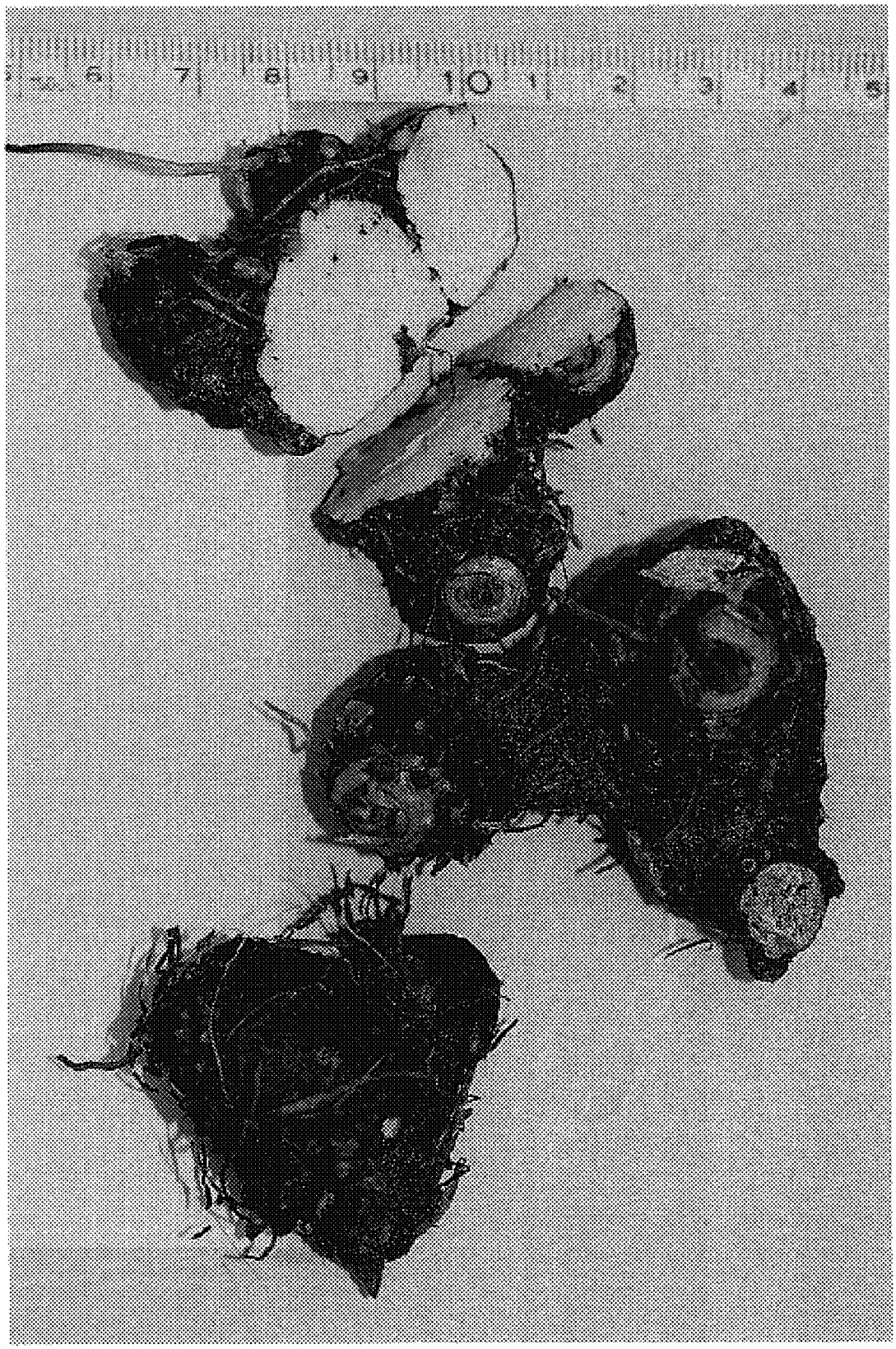
6
7
8
9
10
1
2
3
4
5